(12) United States Patent
Fenster et al.

(10) Patent No.: US 12,380,996 B2
(45) Date of Patent: Aug. 5, 2025

(54) REMOTE MANAGEMENT OF DEVICE USER INTERFACE CONTENT

(71) Applicant: Welch Allyn, Inc., Skaneateles Falls, NY (US)

(72) Inventors: Douglas Paul Fenster, Onondaga Hill, NY (US); Robert Christopher Rogers, Syracuse, NY (US); Alexander Dennis Fries, Camillus, NY (US); Allen R. Hart, Knoxville, TN (US); Eric P Jensen, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 119 days.

(21) Appl. No.: 18/183,665

(22) Filed: Mar. 14, 2023

(65) Prior Publication Data

US 2023/0298742 A1 Sep. 21, 2023

Related U.S. Application Data

(60) Provisional application No. 63/320,636, filed on Mar. 16, 2022.

(51) Int. Cl.
*G16H 40/40* (2018.01)
*G06F 8/65* (2018.01)

(52) U.S. Cl.
CPC .............. *G16H 40/40* (2018.01); *G06F 8/65* (2013.01)

(58) Field of Classification Search
CPC ........... G16H 40/40; G16H 40/43; G06F 8/65
See application file for complete search history.

(56) References Cited

U.S. PATENT DOCUMENTS

| | | | |
|---|---|---|---|
| 6,685,637 | B1 | 2/2004 | Rom |
| 7,970,944 | B2 | 6/2011 | Pena et al. |
| 10,896,051 | B2 | 1/2021 | Krishnasamy et al. |
| 11,210,119 | B2 | 12/2021 | Dong |
| 2011/0009813 | A1* | 1/2011 | Rankers ............ G06Q 30/0255 345/173 |

(Continued)

FOREIGN PATENT DOCUMENTS

| | | |
|---|---|---|
| CN | 102981851 | 3/2013 |
| CN | 110457085 | 11/2019 |

(Continued)

OTHER PUBLICATIONS

The Extended European Search Report mailed Jul. 19, 2023 for the European Patent Application No. 23162279.6, 10 pgs.

(Continued)

*Primary Examiner* — Ziaul A Chowdhury
(74) *Attorney, Agent, or Firm* — Lee & Hayes, P.C.

(57) ABSTRACT

Software of devices, such as medical devices or other constrained devices configured to implement specific functions, can use content files to determine text strings or other content values to present in association with user interface elements. Devices can receive relevant content files, such as new versions of previously-stored content files or new content files containing text in different languages, from a remote content file repository. The software of the devices can accordingly update content values presented in user interfaces based on newly received content files, without the software being re-coded, the software being restarted, or the devices rebooting.

20 Claims, 5 Drawing Sheets

(56) References Cited

U.S. PATENT DOCUMENTS

| | | | | |
|---|---|---|---|---|
| 2011/0126098 A1* | 5/2011 | Jellison, Jr. | ............ | G06F 40/58 |
| | | | | 704/E13.011 |
| 2017/0139577 A1* | 5/2017 | Pesarese | ............ | G06F 3/04847 |
| 2017/0293495 A1* | 10/2017 | Caunter | ............ | G06F 9/44505 |
| 2021/0173681 A1* | 6/2021 | Dong | ...................... | G06F 9/454 |
| 2023/0070842 A1* | 3/2023 | Wei | ........................ | G06F 40/30 |

FOREIGN PATENT DOCUMENTS

| | | |
|---|---|---|
| CN | 110647376 | 1/2020 |
| CN | 110716777 | 1/2020 |
| WO | WO2017016179 | 2/2017 |

OTHER PUBLICATIONS

Office Action for European Application No. 23162279.6, Dated Apr. 22, 2024, 4 pages.

\* cited by examiner

| Content File 110A | |
|---|---|
| Content ID 202 | Content Value 204 |
| 1 | "Yes" |
| 2 | "No" |
| 3 | "Okay" |
| 4 | "Hello" |
| 5 | "Cancel" |
| ... | ... |

| Content File 110B | |
|---|---|
| Content ID 202 | Content Value 204 |
| 1 | "Yes" |
| 2 | "No" |
| 3 | "OK" |
| 4 | "Welcome" |
| 5 | "Cancel" |
| ... | ... |

| Content File 110C | |
|---|---|
| Content ID 202 | Content Value 204 |
| 1 | "Sí" |
| 2 | "No" |
| 3 | "OK" |
| 4 | "Bienvenido" |
| 5 | "Cancelar" |
| ... | ... |

REMOTE MANAGEMENT OF DEVICE USER INTERFACE CONTENT

RELATED APPLICATIONS

This U.S. Patent Application claims priority to provisional U.S. Patent Application No. 63/320,636, entitled "REMOTE MANAGEMENT OF DEVICE USER INTERFACE CONTENT," filed on Mar. 16, 2022, the entirety of which is incorporated herein by reference.

TECHNICAL FIELD

The present disclosure relates to user interfaces of devices, and more particularly to remotely updating user interface content presented by devices.

BACKGROUND

Medical devices, diagnostic devices, or other types of devices may be embedded computing devices, constrained devices, or other computing devices that include processors, memory, and/or other computing elements, and that can present a user interface on a screen or other display. Such devices may execute software, such as firmware, operating systems, and/or applications, that can render the user interface and/or determine content to present within the user interface.

Conventionally, content for a user interface of a device can be defined within software code executed by the device. For example, firmware of a device may be hard-coded to display specific text in association with specific user interface elements. Accordingly, to change text strings or other user interface content displayed by such a device, a new version of device software that includes altered lines of code defining the user interface content changes can be created and tested, be delivered to the device, and be installed on the device.

However, conventional methods of changing user interface elements by creating and installing new software versions on devices can lead to delays, inconsistencies between devices, and other issues. For example, if firmware of a device is hard-coded to use a particular text string in a user interface, changing that text string in the user interface may require a new version of the firmware to be installed on the device that has been coded to include an altered version of the text string. Although the change to the text string in the firmware code may be relatively small, for instance to change a single word or to fix a typographical error in some cases, it may take weeks or months for the new firmware code version to be fully tested for compliance with rules and regulations that apply to the device. For example, regulations for medical devices may require exhaustive testing for new firmware versions, such that a manufacturer may have to go through such testing even if the only change relative to a previous firmware version is an adjustment of user interface text. This process may be further lengthened if a manufacturer produces multiple types and/or models of devices, and has to individually re-code and test software for each device type and/or model in order to make user interface changes that are consistent across the devices.

Additionally, conventional software updates may have to be delivered to devices and installed on the devices. Installing new software, such as a new firmware version that includes changes to user interface text or other user interface content, on a device may involve a reboot of the device. Accordingly, users may be unable to use a device for its primary purpose during a firmware update or other software update that includes changes to user interface content.

Hard-coding specific user interface content into device software can also delay device production and/or shipping of the devices to end-users. For example, a manufacturer may have to delay shipping a device until corresponding device software that includes specific user interface content in numerous languages that users may potentially use has been fully coded and tested. In many cases users of a particular device may be likely to only view user interface content in one or two of those languages, such that waiting to ship the device until software with hard-coded text in numerous languages is ready can lead to delays and increase the size of software code stored in memory on the device.

The example systems and methods described herein may be directed toward mitigating or overcoming one or more of the deficiencies described above.

SUMMARY

Software of devices, such as medical devices or other constrained devices configured to implement specific functions, can use content files to determine text strings or other content values to present in association with user interface elements. Devices can download or receive relevant content files, such as new versions of previously-stored content files or new content files containing text in different languages, from a remote content file repository. The software of the devices can accordingly update content values presented in user interfaces based on newly received content files, without the software being re-coded, re-tested, and/or re-validated, and/or without restarting the software or rebooting the devices.

According to a first aspect, a method includes presenting, via software executing on a medical device, user interface elements of a user interface. The software determines content values to display in association with the user interface elements based at least in part on first content values indicated by a first content file stored in memory of the medical device. The method also includes loading a second content file into the memory of the medical device during execution of the software. The second content file is provided by a content file repository remote from the medical device, and indicates second content values associated with the user interface elements. The method further includes updating, via the software executing on the medical device, the content values displayed in association with the user interface elements based at least in part on the second content values indicated by the second content file. The content values displayed in association with the user interface elements are updated, based at least in part on the second content values indicated by the second content file, without upgrading the software, restarting the software on the medical device, or rebooting the medical device.

According to a second aspect, a medical device includes one or more processors and memory. The memory stores computer-executable instructions associated with software that, when executed by the one or more processors, cause the one or more processors to perform operations. The operations include presenting user interface elements of a user interface. Content values displayed in association with the user interface elements are determined based at least in part on first content values indicated by a first content file stored in the memory. The operations also include loading a second content file into the memory. The second content files are provided by a content file repository remote from the medical device, and indicates second content values associated with the user interface elements. The operations further include updating the content values displayed in association with the user interface elements based at least in part on the second content file. The content values displayed in association with the user interface elements are updated, based at least in part on the second content values indicated by the second content file, without upgrading the software, restarting the software on the medical device, or rebooting the medical device.

According to a third aspect, one or more non-transitory computer-readable media store computer-executable instructions that, when executed by one or more processors of a medical device, cause the one or more processors to perform operations. The operations include determining user interface elements to display in a user interface associated with the medical device. The operations also include determining content identifiers associated with the user interface elements. The operations further include determining first content values, associated with the content identifiers, indicated in a first content file stored locally on the medical device, and displaying the first content values, in association with the user interface elements, based on the first content file. The operations additionally include receiving a second content file downloaded from a content file repository, indicating second content values associated with the content identifiers. The operations also include updating the user interface, without rebooting the medical device or changing the computer-executable instructions, to display the second content values in association with the user interface elements.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
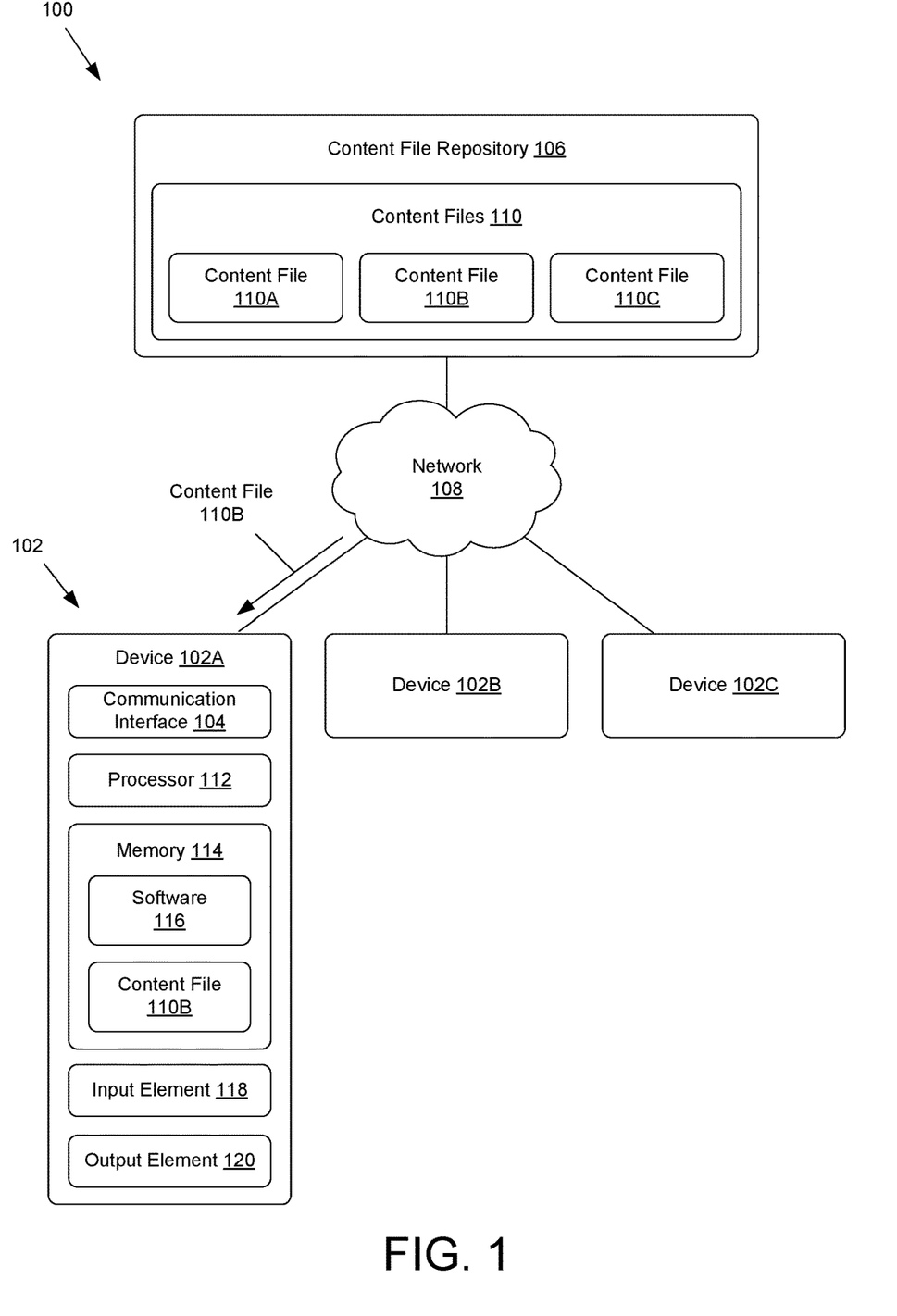
FIG. 1 shows an example of a system for remotely updating user interface content on one or more devices.

FIG. 1 shows an example of a system 100 for remotely updating user interface content on one or more devices 102. The devices 102 can include at least one communication interface 104 that allows the device to be in at least occasional data communication with a content file repository 106 via a network 108, and/or include data ports, memory card slots, or other interfaces that allow data from the content file repository 106 to be provided to the devices 102 via intermediate computing devices, removable storage units, or other data delivery mechanisms. The content file repository 106 can store content files 110, such as content files 110 containing text strings, icons or other graphical elements, audio data, animation data, and/or other types of content that can be presented via user interfaces associated with the devices 102. As described further below, the content file repository 106 can transmit content files 110 to the devices 102 via the network 108, and/or the devices 102 can receive content files 110 provided by the content file repository 106 via intermediate computing devices, removable storage units, or other data delivery mechanisms. The devices 102 can accordingly use content files 110, provided by the content file repository 106, to adjust content presented by the devices 102 via user interfaces, for example without installing new software that includes hard-coded changes to user interface content, without restarting software executed by the devices 102, and/or without rebooting the devices 102.

Each of the devices 102 can be a computing device that includes at least one processor 112 and memory 114. The devices 102 can also each include the communication interface 104 that allows the devices 102 to communicate with the content file repository 106 via the network 108, and/or other interfaces by which the devices 102 can receive content files 110 from other computing devices, removable storage units, and/or other data delivery mechanisms. The processor 112 of each device can perform at least some data processing to implement functions of the device, and/or to present information via a user interface as described herein.

As described further below, the devices 102 may be embedded and/or constrained devices, such as medical devices or other specialized computing devices designed to perform specific functions. For instance, in some examples, the devices 102 can be "smart" medical or diagnostic devices, such vision screening devices, cameras, otoscopes, blood pressure monitors, other types of patient monitoring devices, medical screening devices, and/or other types of devices. In other examples, the devices 102 can be other types of sensors, smart devices, Internet of Things (IoT) devices, or other devices. The devices 102, such as device 102A, device 102B, and device 102C shown in FIG. 1, can include instances of the same type of device or include multiple types of devices. For example, the devices 102 can include one or more models of a particular device type, or include multiple models and/or device types.

The memory 114 of a device can store computer-implemented instructions and/or other data associated with software 116 executed by the processor 112 of the device. As described further below, such data stored in the memory 114 of a device can include code and data associated with the software 116 itself, as well as one or more separate content files 110 that can be used by the software 116. The software 116 can include firmware of the device, an operating system of the device, one or more applications that the device can execute, or other types of software that can be executed by the device. As described further below, the device can be a medical device, or other embedded or constrained device, that may have a smaller amount of memory than a general purpose computer or other types of computing devices. Accordingly, the size of the memory 114 of the device may be sufficient to store data associated with device firmware and/or primary applications associated with specific functions of the device as well as a limited number of content files 110, such as up to five content files 110 or any other maximum number of content files 110. However, the size of the memory 114 may not be sufficient to store additional data beyond the firmware and/or primary applications associated with specific functions of the device and the limited number of content files 110.

The software 116 that executes on a device can be configured to use one or more content files 110, stored in the memory 114 of the device, to present information via a user interface. The content files 110 can be default content files 110, and/or content files 110 provided by the content file repository 106 that are loaded into memory 114 of the device via the network 108 and/or other data delivery mechanisms.

As described herein, individual devices 102 can download or receive one or more specific content files 110 from the content file repository 106, such as content files 110 containing text strings in different languages, updated versions of text strings that change words, phrases, web links, and/or other text, new or alternate graphical elements, new or alternate audio data, new or alternate animation data, or any other type of content. As an example, if the content file repository 106 stores a set of content files 110 that includes content file 110A, content file 110B, and content file 110C, the device 102A may download content file 110B from the content file repository 106 and store content file 110B in the memory 114 of device 102A as shown in FIG. 1. The software 116 of each device can use such downloaded content files 110 to display corresponding content in a user interface, without the software 116 itself being updated, re-installed, or restarted, and/or without the device being rebooted.

The content file repository 106 can be a server, database, cloud computing element, or other data storage location that can store and maintain content files 110, and that can transfer individual content files 110 to individual devices 102 over the network 108. For example, the content file repository 106 may have an Application Programming Interface (API) or other interface that allows devices 102 to query the content file repository 106 for content files 110 and/or to receive content files 110 from the content file repository 106.

The content file repository 106 can be owned or operated by an entity that manufactures the devices 102, and/or sells or otherwise provides the devices 102 to users. The entity, such as a manufacturer of the devices 102, can generate new and/or updated content files 110 over time, and can load the content files 110 to the content file repository 106. Accordingly, the devices 102 can receive new or updated content files from the content file repository 106 over the network 108 after the devices 102 have been sold or deployed in the field. For example, over time the entity may develop new content files 110 that contain text strings in different languages, and/or create new versions of previously-existing content files 110 that alter text strings or other content values provided in the content files 110. The entity can add the new or updated content files 110 to the content file repository 106, such that the new or updated content files 110 become available to the devices 102.

In some examples, one or more default content files 110 may initially be loaded into the memory 114 of a device when the device is manufactured or provisioned before being shipped or deployed in the field. However, in some situations the device may overwrite a default content file stored in the memory 114 with another content file received from the content file repository 106. For instance, the device may receive a newer version of a default content file from the content file repository 106, and overwrite the default content file with the newer version received from the content file repository 106. In other situations, the device may store a content file received from the content file repository 106 in the memory 114 in addition to default content file previously stored in the memory 114. For instance, if a default content file stored in the memory 114 is an English content file containing English text strings, the device may receive a separate Spanish content file containing Spanish text strings from the content file repository 106, and store the Spanish content file in the memory 114 in addition to the default English content file.

Similarly, in some situations a device may overwrite any other content file previously-stored in the memory 114 of the device with another content file received from the content file repository 106. For instance, at a first time, a device may receive a first version of a content file from the content file repository 106, and store the first version of the content file in the memory 114. At a second time, the device may receive a second version of the content file from the content file repository 106, and replace the first version of the content file with the second version of the content file in the memory 114. In other situations, the device may store a content file received from the content file repository 106 in the memory 114 in addition to one or more other content files previously received from the content file repository 106.

The devices 102 can, in some examples, be embedded devices or constrained devices that are designed to perform specific functions. For example, the devices 102 can be medical devices that are configured to perform particular patient monitoring or diagnostic functions. The processor 112, memory 114, and/or other computing resources of such embedded devices or constrained devices may be less powerful and/or more limited than computing resources of general purpose computers, smartphones, or other types of computing devices. For instance, while a general purpose computer may have a relatively large hard drive, such that users can store large amounts of user data or install numerous applications, the memory 114 of the devices 102 may be smaller and/or be sized to store relatively small amounts of data that the devices 102 use to perform specific operations. Accordingly, the memory 114 of each of the devices 102 may be limited in size, and have enough space to store a relatively small number of content files 110, such as one content file, two content files, three content files, or any other relatively small number of content files, in addition to the software 116 and/or other data stored in the memory 114.

As a non-limiting example, if the device 102A is a type of patient monitoring device, the memory 114 of device 102A may be sized to store software 116 and data that device 102A uses to implement specific patient monitoring operations. The memory 114 of the device 102A may also have sufficient space to store up to five content files 110, or any other relatively small maximum number of content files 110, in addition to the software 116 and/or other data that device 102A uses to implement the patient monitoring operations. However, in some situations the content file repository 106 may store tens or hundreds of different content files 110, such that the memory 114 of device 102A may only have enough space to store a relatively small percentage of the total number of content files 110 available from the content file repository 106.

As discussed above, the devices 102 can have at least one communication interface 104, such as a network interface or other data communication interface, that allows the devices 102 to connect to the network 108. The network 108 can include the Internet and/or other data networks. Different types of devices 102 may have different types of communication interfaces. For example, some devices 102 can have Ethernet, Wi-Fi®, cellular, and/or other wired or wireless data connections that allow the devices to directly connect to the network 108 and communicate with the content file repository 106. However, other devices 102 may have Bluetooth® connections, or other wired or wireless connections, by which the devices 102 can connect to Internet-connected computers or other intermediate devices that can connect to the network 108. In these examples, such devices 102 can access the network 108 and the content file repository 106 when the devices 102 are tethered to, or are otherwise connected to, other intermediate devices that have connections to the network 108.

In some examples, communication interfaces of some devices 102 may also, or alternately, include a memory card reader, Universal Serial Bus (USB) port, or other removable storage interface, by which the devices 102 can receive content files 110 that have been downloaded from the content file repository 106 by other devices 102, computers, or other computing elements. For example, an Internet-connected computer may download a content file from the content file repository 106, and load the content file onto a removable storage unit, such as a USB flash drive or a memory card. A user may then physically transfer the removable storage unit to one of the devices 102 and attach the removable storage unit to a removable storage interface of the device, such that the memory 114 of the device can receive the content file downloaded from the content file repository 106 via the removable storage unit. As another example, an Internet-connected computer may download a content file from the content file repository 106, and a user may then connect the Internet-connected computer to one of the devices 102 via an Ethernet cable, a USB cable, a Bluetooth® connection, or other data interface, such that the memory 114 of the device can receive a copy of the content file that the Internet-connected computer downloaded from the content file repository 106.

Individual devices 102 can include, or be associated with, at least one input element 118, such as a camera, a scanner, a sensor, or other type of input element. Different types of devices 102 may have different types of input elements. For example, a vision screening device may have one or more input elements that include a camera or other optical input sensor, while a blood pressure monitor may have one or more input elements that include a blood pressure sensor. In some examples, the input elements of a device can also include a keyboard, mouse, touchscreen, buttons, switches, and/or other user input devices that a user can use to operate the device.

Individual devices 102 can also include, or be associated with, at least one output element 120, such as a screen, a speaker, a printer, or other type of output element. The output element 120 associated with a device can present a user interface. As described herein, content of the user interface presented via the output element 120 can be based, at least in part, on one or more content files 110 stored in the memory 114 of the device, such as a content file received from the content file repository 106.

Different types of devices 102 may have different types of output elements. For example, some devices 102 may have integrated screens, speakers, printers, and/or other types of output devices. Accordingly, such devices 102 can directly present user interface content via such integrated output elements, for instance by displaying user interface information on an integrated screen or by printing user interface information via an integrated printer. However, other devices 102 may connect to external output elements, such as external monitors, external printers, external devices, or other external output elements. As an example, a device without an integrated screen may use the communication interface 104 of the device to pair with a mobile phone, such that the device can use a screen of the mobile phone as the output element 120, and the device can display a user interface via the screen of the mobile phone.

In some examples, content files 110 that are stored at the content file repository 106, and/or can be stored on and used by the devices 102, can be data files, such as JavaScript Object Notation (JSON) files, Extensible Markup Language (XML) files, comma-separated value (CSV) files, or other types of data files. In other examples, the content files 110 can be other types of data elements, such as database data, binary data, data objects, a binary large object (BLOB), or other types of data elements or data structures.

A content file can include attribute-value pairs or other data that indicate specific content values associated with corresponding user interface elements. For example, user interface elements that can be rendered, displayed, or presented by the software 116 can be associated with corresponding content identifiers. User interface elements can include buttons, labels, fields, and/or other user interface elements. A content file can indicate specific content values associated with one or more content identifiers, such as text strings, graphics, audio data, animation data, or other content values. Accordingly, the software 116 can be configured to determine content identifiers of particular user interface elements that are to be presented in a user interface, locate content values associated with those content identifiers in one or more content files 110, and use the content values from the content files 110 to present the particular user interface elements.

For example, a particular content file may include a set of text strings that may be displayed in user interfaces of one or more devices 102. Each of the text strings in the content file may be associated with a corresponding content identifier. Code of software 116 that executes on one or more devices 102 can reference content identifiers in association with individual user interface elements, such that the software 116 can use content identifiers to retrieve the corresponding text strings from the content file. For instance, software 116 executing on device 102A may determine that a confirmation button is to be rendered in a user interface shown on a screen of device 102A. Code of the software 116 may be configured to identify situations in which a confirmation button is to be displayed in the user interface, but may not indicate specific text to display within the confirmation button. However, the code of the software 116 may indicate that the confirmation button is associated with a particular content identifier. The device 102A may have content file 110B in memory 114, as shown in FIG. 1. Content file 110B may indicate that a text string of "OK" is associated with the particular content identifier that is also associated with the confirmation button. Accordingly, the software 116 can use the particular content identifier to retrieve the "OK" text string from the content file 110B, and render a confirmation button that displays the "OK" text string.

Different content files 110 may indicate different values for the same content identifier. For instance, while content file 110B may indicate that a text string of "OK" is associated with the particular content identifier discussed in the example above, content file 110A may indicate that a text string of "Okay" is associated with the same content identifier. Accordingly, if device 102A had content file 110A in memory 114 instead of content file 110B in the example discussed above, the software 116 could have retrieved the "Okay" text string from content file 110A and rendered a confirmation button that displayed the "Okay" text string instead of the "OK" text string. Other examples of differences between content files 110 are discussed further below with respect to FIG. 2.

As discussed above, in some examples the devices 102 may include different devices types and/or device models. However, the user interfaces associated with different device types and/or model types may have the same or similar types of user interface elements. For example, user interfaces associated with devices produced by the same manufacturer may include the same, or similar, types of buttons, icons, messages, graphics, sounds, animations, and/or other user interface elements. Accordingly, in some examples, content files 110 that include content values that may be used by multiple models and/or types of devices 102 can be provided by the content file repository 106.

As a non-limiting example, a manufacturer may produce vision screening devices and blood pressure monitors. Although vision screening devices and blood pressure monitors may be designed to perform different medical tasks, the user interfaces associated with the vision screening devices and blood pressure monitors may have some consistent user interface elements, such as identical confirmation buttons. The vision screening devices and blood pressure monitors may have been shipped with default content files 110 that cause the devices to display "Okay" in confirmation buttons. However, if the manufacturer later chooses to change its user interface style from using "Okay" to using "OK" across all of its devices, the manufacturer can add a new content file to the content file repository 106 that includes an "OK" text string instead of an "Okay" text string. The vision screening devices and blood pressure monitors can, opportunistically and without impacting usability of the devices, download the new content file from the content file repository 106 such that the new content file causes the software 116 of the vision screening devices and blood pressure monitors to each begin displaying "OK" in confirmation messages in accordance with the manufacturer's updated user interface style. In this example, although the software 116 of the vision screening devices and blood pressure monitors may be different, and implement different medical tasks, the new content file can alter the text of confirmation messages displayed in user interfaces by the software 116 without changes to the software 116 itself.

In some examples, content files 110 stored at the content file repository 106 may contain a master set of text files, or other types of content, that can be used by any device. For instance, a most recent version of a content file that can be downloaded or received by any device can include a master set of 500 text strings. The software 116 of different devices may be configured to use different subsets of that master set of text strings. For example, software 116 of device 102A may be configured to use content identifiers that correspond to a subset of 300 text strings, within the master set of 500 text strings, to retrieve content values to display in a user interface of device 102A. However, software 116 of device 102B may be configured to use content identifiers that correspond to a different subset of 200 text strings, within the master set of 500 text strings, to retrieve content values to display in a user interface of device 102B. In this example, device 102A and device 102B may each receive the same content file from the content file repository 106 that includes the most recent master set of text files, but device 102A and device 102B may use different subsets of those text files in corresponding user interfaces.

In other examples, some content files 110 available at the content file repository 106 may be specific to certain types and/or models of devices. For instance, if a user interface for a particular type of device may use a text string that is specific to that type of device, and that user interfaces of other types of devices may not be likely to use, the text string may be included within a content file associated with that particular type of device. Accordingly, instances of that type of device may download or receive the device-specific content file from the content file repository 106, while other types of devices may not download or receive the device-specific content file from the content file repository 106. In some examples, such device-specific content files 110 may be downloaded, received, and/or used by devices 102 in addition to, or instead of, one or more other content files 110 that include master sets of text files or other content values that may be used by multiple types or models of devices.

The content files 110 stored at the content file repository 106 may be associated with version numbers. As a non-limiting example, content file 110A and content file 110B may both contain English text strings, but content file 110B may be a more recent version of content file 110A that includes changes or corrections to English text strings that were included in content file 110A. In these examples, devices 102 and/or the content file repository 106 may compare version numbers of content files 110 currently stored in memory 114 by individual devices 102 against the version numbers of corresponding content files 110 stored at the content file repository 106. Accordingly, the content file repository 106 can provide the most recent versions of content files 110 to individual devices 102, and/or can avoid providing devices 102 with content files 110 if the devices 102 already have the most recent versions of the content files 110. In some examples, when a new version of a content file is added to the content file repository 106, an older version of the content file can be archived or removed from the content file repository 106, such that only the most recent version of the content file is available to devices 102 at the content file repository 106.

Different content files 110 stored at the content file repository 106 may also be associated with different languages. For example, content file 110B may include a set of English text strings, and content file 110C may include a set of Spanish text strings. In this example, devices 102 that are located in English-speaking countries, or for which user preference settings indicate that users of the devices 102 want to read user interface elements in English, can download, receive, and/or use content file 110B. However, other devices 102 that are located in Spanish-speaking countries, or for which user preference settings indicate that users of the devices 102 want to read user interface elements in Spanish, can download, receive, and/or use content file 110C. In this example, the software 116 of a device located in an English-speaking country may be identical to the software 116 of a similar device located in a Spanish-speaking country, and may associate the same content identifiers with the same user interface elements. However, a device that receives and uses content file 110B can use an English version of a text string to display a particular user interface element, while another device that receives and uses content file 110C can use a corresponding Spanish version of the text string to display the same particular user interface element.

Individual devices 102 may determine which language-specific content files 110 to obtain from the content file repository 106 based on user settings, device location data, Internet Protocol (IP) address information, and/or other data. In some examples, a device may display a user interface with content presented in a default or currently-selected language, based on a current content file stored in memory 114 of the device. However, a user can use the user interface to select a preference for a different language. The device can accordingly request the most recent version of a content file corresponding to the user-selected language from the content file repository 106, such that the device can begin using the user-selected language to display content in the user interface.

In other examples, a device may include a Global Positioning System (GPS) sensor or other type of location sensor that can indicate a location of the device, and/or an IP address, a business or registration address, or other data may indicate a location of the device. If location data associated with the device indicates that the device is currently located in a particular country or area, the device may request the most recent version of a content file corresponding to a language frequently spoken in that country or area. Accordingly, the device can use a local language content file to automatically begin using the local language to display content in the user interface, and/or to make settings to change the user interface to the local language available to be selected by users. As a non-limiting example, a particular device may be provisioned at a factory with the only content file in memory 114 of the device being a default English-language content file, but the device may later be shipped to Paris, France. If GPS data, IP address data, device registration data, and/or other location data indicates that the device has been moved to France, the device may automatically request a most-recent French-language content file from the content file repository 106, as it may be likely that users of the device in France will want to read French text in the user interface of the device.

In some examples, the devices 102 can be configured to periodically or occasionally query the content file repository 106, via the network 108, to determine whether the content file repository 106 stores any content files 110 that are relevant to the devices 102 and that the devices 102 should download. For example, the devices 102 can query the content file repository 106 to determine whether the content file repository 106 stores new versions of content files 110 already stored in memory 114 by the devices 102. As another example, the devices 102 can query the content file repository 106 to determine whether the content file repository 106 stores any other content files 110 that may be relevant to the devices 102, such as content files 110 associated with particular languages as described above.

The devices 102 can be configured to query the content file repository 106 for new relevant content files 110 once per hour, once per day, once per week, or on any other scheduled basis. The devices 102 can also, or alternately, be configured to query the content file repository 106 in response to trigger events. For instance, a device may query the content file repository 106 when the device is powered on, when the device becomes connected to the network 108, and/or in response to a user instruction to check for updates to content files 110. As another example, if one or more new content files 110 are added to the content file repository 106, the content file repository 106 may send a notification to the devices 102 over the network 108. The notification may instruct the devices 102 to query the content file repository 106 at the next opportunity for each device, for instance to determine whether the new content files 110 are relevant to the individual devices 102.

In some examples, the devices 102 can be configured to query the content file repository 106 and/or download content files 110 during periods in which the devices 102 are otherwise idle, but have a connection to the network 108. For instance, if a device is a patient monitoring device or other type of medical device, the device may wait for an idle period during which the device is not actively being used for medical tasks, and then query the content file repository 106 and/or download content files 110 during the idle period if the device is connected to the network 108.

While devices 102 may query the content file repository 106 and/or download content files 110 during times when the devices 102 have direct or indirect connections to the network 108 as described above, in some examples content files 110 can also be delivered to devices 102 via removable storage units. For example, a computer or other separate device can query the content file repository 106 for new content files 110, download new content files 110, and transfer downloaded content files 110 to a USB flash drive, memory card, or other removable storage unit. The removable storage unit can then be transferred to one or more devices 102 that do not have network connections, such that the devices 102 can receive downloaded content files 110 via the removable storage unit. Similarly, a computer or other separate device can query the content file repository 106 for new content files 110, download new content files 110, and transfer downloaded content files 110 to devices 102 via local wired or wireless data connections.

In some examples, the content files 110 provided by the content file repository 106 can be encrypted, and/or can be transferred to the devices 102 over secure network connections. Accordingly, devices 102 may perform decryption operations and/or validation operations on downloaded content files. For instance, the software 116 of a device may be configured to use a decryption key or other cipher to decrypt a received content file, and/or verify that the received content file matches a hash code. Additionally, if a received content file is a replacement for a content file already stored in memory 114 of a device, the device can be configured to verify that a version number of the newly received content file is greater than the version number of the current content file before overwriting the current content file with the new content file in the memory 114.

In some examples, individual devices 102 may each store a local master content file in memory 114, and may update the local master content file based on new or updated content files 110 received from the content file repository 106. For example, a device may have a local master content file that includes a series of attribute-value pairs defining content values associated with content identifiers. In this example, the device may receive a first content file from the content file repository 106 that includes additional content identifiers and corresponding content values. Accordingly, the device can edit its local master content file to add the additional content identifiers and corresponding additional content values based on the newly received first content file. If the device later receives a second content file from the content file repository 106 that adjusts the content values associated with any of the content identifiers in the local master content file, such as any of the content identifiers that were initially in the local master content file or that were added to the local master content file based on the first content file, the device can edit corresponding entries in the local master content file based on the second content file.

After a device receives a new content file from the content file repository 106, the software 116 of the device can use the new content file to determine content to present in a user interface of the device. For example, as discussed above, the software 116 can be configured to display user interface elements that are associated with content identifiers, based on separate content files 110 stored in the memory 114 of the device that indicates content values that correspond to the content identifiers associated with the user interface elements. Accordingly, as soon as the device receives a new content file that includes content values associated with those content identifiers, the software 116 can use the new content file to retrieve content values associated with user interface elements, and present those content values in a user interface. Because the software 116 itself has not changed, the software 116 can use new content values provided in a newly received content file almost immediately, without the device being rebooted, without the software 116 being restarted, and without a new version of the software 116 being installed on the device. In some examples, the software 116 may be configured to wait until the device is in an idle state before updating user interface elements based on a newly received content file, to avoid confusing a user by adjusting user interface elements while the device is in active use.

Overall, the systems and methods described herein can allow user interfaces associated with devices 102 to be updated based on new or different content files 110, without developing or installing new versions of software 116 for the devices 102, and without the devices 102 being rebooted or restarting the software 116. As a non-limiting example, to update a text string displayed in a user interface button presented by a device, a manufacturer of the device can generate a new content file that includes an updated text string, and can upload the new content file to the content file repository 106. The software 116 of the device can check the content file repository 106 for new content files, and accordingly download the new content file. The software 116 of the device can directly use the new content file to identify the updated text string, and use the updated text string to present the updated text string in association with the user interface button, without the software 116 itself being updated or restarting, and without the device being rebooted.

Accordingly, the text displayed on the user interface button can be updated via a new content file, without the software 116 having to be re-coded, re-tested, deployed to the device, and installed on the device. The text displayed on the user interface button can also be updated via a new content file, without the device having to be restarted or rebooted. For some types of devices 102, such as medical devices, that may have relatively stringent standards for developing and testing new software versions, the systems and methods described herein can allow user interface changes to be implemented more quickly than by re-coding software 116 to include hard-coded changes to user interface elements. For instance, because the software 116 of a device can be configured to determine content values for user interface elements based on content files 110, the software 116 can update user interface content based on new content files 110 without changes to the software 116 itself that might require testing.

In some examples, the systems and methods described herein can also allow devices 102 to be provisioned with a single default content file, or other relatively small set of default content files 110, before being shipped or deployed in the field. For instance, a device can be shipped with a default English-language content file, but may not have any other content files 110. When a manufacturer develops additional content files 110, such as an updated English-language content file and/or content files for other languages, devices 102 that have already been shipped and deployed in the field can receive those content files 110 from the content file repository 106. Accordingly, a device manufacturer may not have to wait to ship devices 102 until user interface content in numerous languages is ready.

Additionally, the systems and methods described herein can reduce bandwidth usage by the devices 102. For instance, individual content files 110 may be relatively small in size, relative to new versions of the software 116. Accordingly, by releasing user interface updates via relatively small content files 110 instead of hard-coding user interface changes into new versions of software 116, devices 102 can use less bandwidth over the network 108 to download the content files 110, relative to bandwidth the devices 102 might otherwise use to download updated versions of the software 116.

Examples of content files 110 and how software 116 of devices 102 can receive and use content files 110 are discussed further below with respect to FIGS. 2, 3A-3C, and 4. For example, FIG. 2 shows various example content files 110, and FIGS. 3A-3C show how a user interface of a device may change based on the use of different content files 110.

Figure 2:
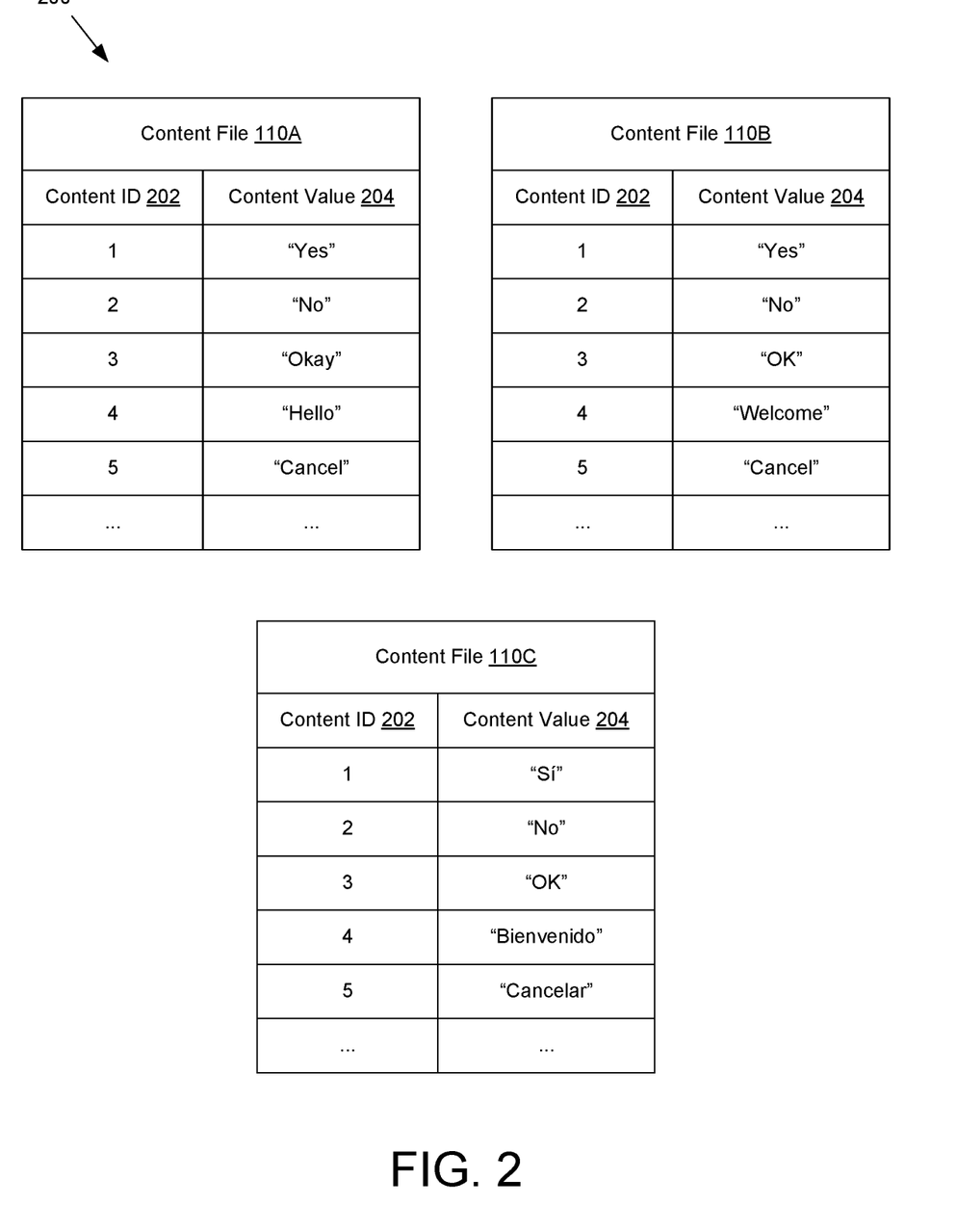
FIG. 2 shows an example of content files that can be stored at a content file repository, and/or that can be used by software of devices to present user interfaces.
Figure 3A:
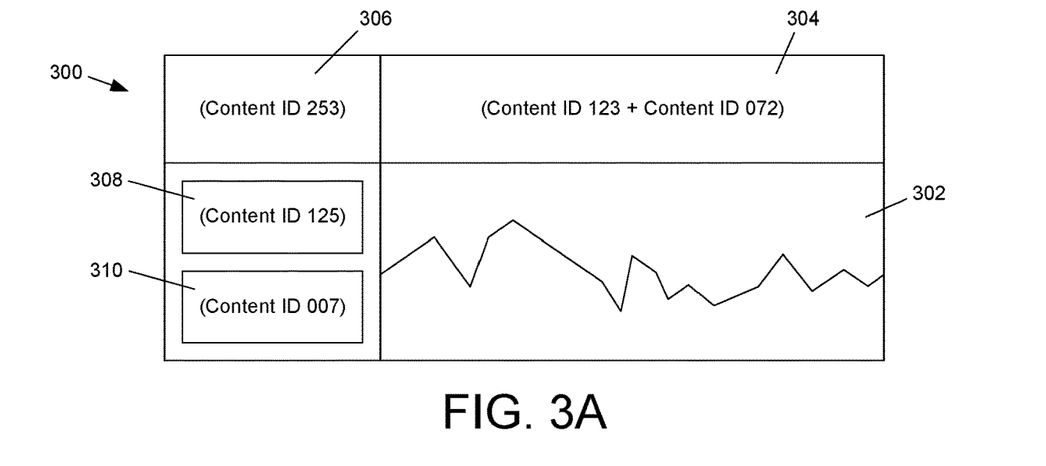
FIGS. 3A-3C show an example of software of a device displaying different user interface content based on different content files.
Figure 3B:
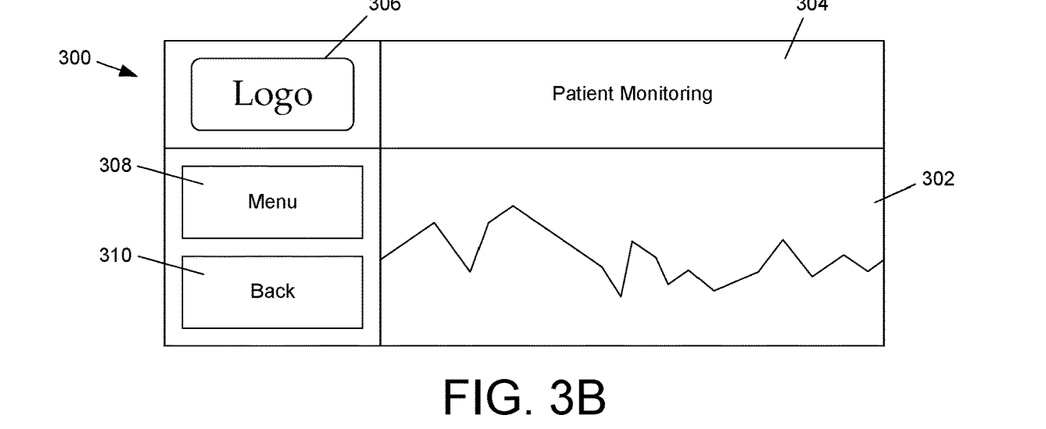
Figure 3C:
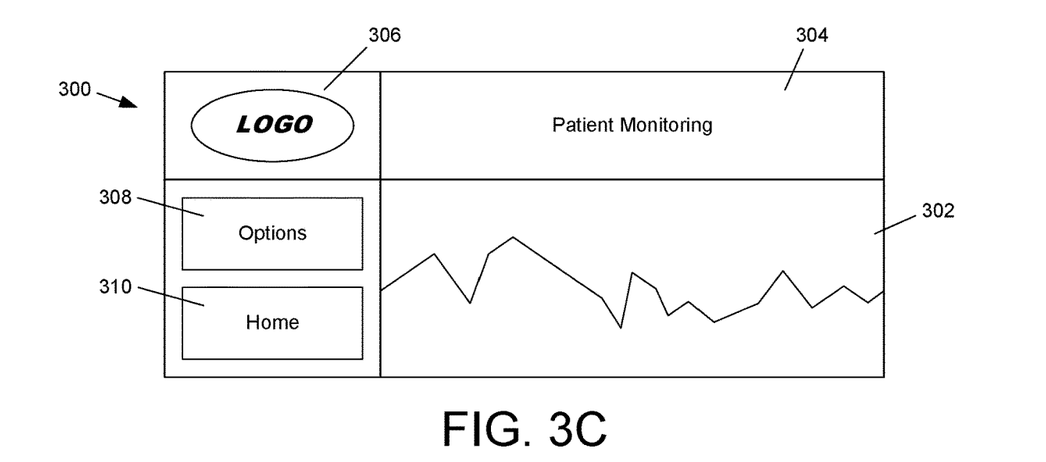

FIG. 2 shows an example 200 of content files 110 that can be stored at the content file repository 106, and/or that can be used by software 116 of devices 102 to present user interfaces. For example, devices 102 may store one or more of the content files 110 by default, and/or receive one or more of the content files 110 from the content file repository 106. The content files 110 can include, for example, content file 110A, content file 110B, and content file 110C. In example 200, content file 110A can be a first version of an English-language content file, while content file 110A can be a second version of an English-language content file. Content file 110C can be a Spanish-language content file. Devices 102 can use, and the content file repository 106 can store and provide, other content files 110, such as content files 110 that contain text strings for other languages, content files 110 that contain images or other graphical data, audio data, animation data, and/or other types of user interface content.

The content files 110 can be structured data files, such as JSON files, XML files, CSV files, or other files that include one or more data pairs. Each data pair can associate a content identifier 202 with a corresponding content value 204. Each content identifier 202 can be a number, alphanumeric character, or any other identifier that the software 116 of one or more devices 102 associates with one or more user interface elements. Individual content files 110 may include the same or different content identifiers. If different content files 110 include the same content identifier 202, the different content files 110 may associate that content identifier 202 with the same or different content value 204. Overall, different content files 110 stored at the content file repository 106 can include one or more differing content values.

As an example, content file 110A can be a first version of an English-language content file that indicates that content identifier "3" is associated with a content value of "Okay," and that content identifier "4" is associated with a content value of "Hello." Accordingly, any devices 102 that store content file 110A by default, or have received content file 110A from the content file repository 106, can display "Okay" in one or more buttons, labels, fields, or other user interface elements that software 116 of the devices 102 associates with content identifier "3." Such devices 102 can similarly use content file 110A to display "Hello" in one or more buttons, labels, fields, or other user interface elements that software 116 of the devices 102 associates with content identifier "4."

However, content file 110B can be a second version of an English-language content file that can be loaded into the content file repository 106 as a replacement for content file 110A. Content file 110B may include at least some different content values relative to content file 110A, such as associating "OK" with content identifier "3" instead of "Okay" and associating "Welcome" with content identifier "4"

instead of "Hello." Any devices 102 that previously stored and used content file 110A may download content file 110B when the devices 102 next query the content file repository 106, or may receive content file 110B via a removable storage unit. Such devices 102 can overwrite content file 110A with content file 110B, or update a local master content file based on content file 110B, in memory 114 of the devices 102. Accordingly, in response to receiving content file 110B, software 116 of the devices 102 can change from displaying "Okay" in user interface elements associated with content identifier "3" based on content file 110A, to displaying "OK" in the user interface elements associated with content identifier "3" based on content file 110B. Similarly, in response to receiving content file 110B, software 116 of the devices 102 can change from displaying "Hello" in user interface elements associated with content identifier "4" based on content file 110A, to displaying "Welcome" in the user interface elements associated with content identifier "4" based on content file 110B.

As another example, content file 110C can be a Spanish-language content file that can be used by software 116 of devices 102 instead of English-language content files 110A and 110B. Content file 110C can indicate that particular content identifiers are associated with Spanish-language text strings. Accordingly, any devices 102 that store content file 110C by default, or have received content file 110C from the content file repository 106, can display Spanish-language text strings in buttons, labels, fields, or other user interface elements that software 116 of the devices 102 associates with the corresponding content identifiers.

For example, while English-language content files 110A and 110B may indicate that content identifier "1" is associated with the English word "Yes," the Spanish-language content file 110C may instead indicate that content identifier "1" is associated with the Spanish word "Si." Accordingly, if software 116 of a device indicates that a user interface element, such as user-selectable button, is associated with a content identifier of "1," the software 116 can use the Spanish-language content file 110C to render the user interface element to display "Si," rather than using an English-language content file to render the user interface element to display "Yes."

In some examples, a device may be provisioned with English-language content file 110A by default. When newer English-language content file 110B becomes available at the content file repository 106, the device may download or receive content file 110B. Software 116 of the device can begin using content file 110B to display English user interface content, without a new version of the software 116 being installed or the device being rebooted. Additionally, or alternately, if GPS data, IP address data, device registration data, or other location data indicates that a particular device is located in Mexico or another location where Spanish is predominantly spoken, or if user input indicates a Spanish-language user preference, the device can download the Spanish-language content file 110C from the content file repository 106, or otherwise receive content file 110C. Accordingly, software 116 of the device may begin using content file 110B to display Spanish user interface content, without a new version of the software 116 being installed or the device being rebooted.

Accordingly, as shown in FIG. 2, a device may use different content files 110 to display different content values in a user interface. An example of software 116 using different content files 110 to adjust a user interface is discussed further below with respect to FIGS. 3A-3C.

FIGS. 3A-3C show an example 300 of software 116 of a device displaying different user interface content based on different content files 110. As described above, the software 116 may be configured to display various user interface elements in different situations, such as buttons, labels, fields, and/or other user interface elements. For example, the software 116 for a patient monitoring device can be configured to display a chart 302, a title bar 304, a logo 306, a first button 308, and a second button 310.

The chart 302 may, for example, display patient data measured or received by the patient monitoring device, such as blood pressure measurements over time or any other type of patient data. The software 116 may be configured to render the chart 302 based on operations of the device without use of a content file.

However, the software 116 can be configured to render other user interface elements, such as the title bar 304, the logo 306, the first button 308, and the second button 310 based on content values indicated in one or more content files. For instance, the software 116 can be configured to associated each of the title bar 304, the logo 306, the first button 308, and the second button 310 with one or more content identifiers, as shown in FIG. 3A. In some examples, the software 116 may associate a particular user interface element, such as the title bar 304, with multiple content identifiers. In these examples, the software 116 can render a user interface element by concatenating different text strings, or otherwise combining multiple content values, associated with the multiple content identifiers in one or more content files 110.

For example, as shown in FIG. 3B, the software 116 of the device can use one or more content files 110 to determine content values associated with the content identifiers the software 116 associates with the title bar 304, the logo 306, the first button 308, and the second button 310. For example, the software 116 may determine that a content file indicates that content values corresponding to the content identifiers of the title bar 304 are "Patient" and "Monitoring," and can combine those content values to display "Patient Monitoring" in the title bar 304 of the user interface. Similarly, the software 116 may determine that the same content file, or one or more other content files, indicates that the content value corresponding to the content identifier of the first button 308 is "Menu" and that the content value corresponding to the content identifier of the second button 310 is "Back," and accordingly render the first button 308 to display "Menu" and the second button 310 to display "Back" as shown in FIG. 3B. The software 116 can also use a content file that contains image data to retrieve an image corresponding to the content identifier of the logo 306, and display that image as the logo 306 in the user interface as shown in FIG. 3B.

At a later point in time, the device may query the content file repository 106 for updated versions of the content files the device currently stores in memory 114, and may download such new content files. The new content files may include different content values for some of the content identifiers that the software 116 associates with user interface elements. Accordingly, the software 116 of the device can change the content of the user interface based on the new content files.

For example, a new content file may indicate that the content value corresponding to the content identifier of the first button 308 is "Options," and that the content value corresponding to the content identifier of the second button 310 is "Home." Accordingly, the software 116 may use the new content file to change the first button 308 from displaying "Menu" (as shown in FIG. 3B based on a previous content file) to displaying "Options" (as shown in FIG. 3C based on the new content file), and change the second button 310 from displaying "Back" (as shown in FIG. 3B based on a previous content file) to displaying "Home" (as shown in FIG. 3C based on the new content file).

In this example, the functionality of the first button 308 coded in the software 116 may be to present a menu of user-selectable options if a user selects the first button 308, and the functionality of the second button 310 coded in the software 116 may be to display a home screen of the device. Although the software 116 can use different content files to change the text displayed on the first button 308 and the second button 310 as shown in FIG. 3B and FIG. 3C, the functionality of the first button 308 and the second button 310 coded in the software 116 can remain unchanged when the software 116 begins using a different content file to determine the content values to present in association with the first button 308 and/or the second button 310.

As another example, the software 116 of the device can have used a first content file containing image data to retrieve a first image corresponding to the content identifier of the logo 306, and to display that first image as the logo 306 in the user interface as shown in FIG. 3B. However, if at a later point in time the device downloads or receives a new content file containing a second image corresponding to the content identifier of the logo 306, the software 116 of the device can change to displaying the second image as the logo 306 in the user interface as shown in FIG. 3C. Accordingly, although the software 116 itself can remain the same, the new content file can cause the software 116 to change the image displayed as the logo 306 without the software 116 being upgraded, the software 116 restarting, or the device rebooting.

Figure 4:
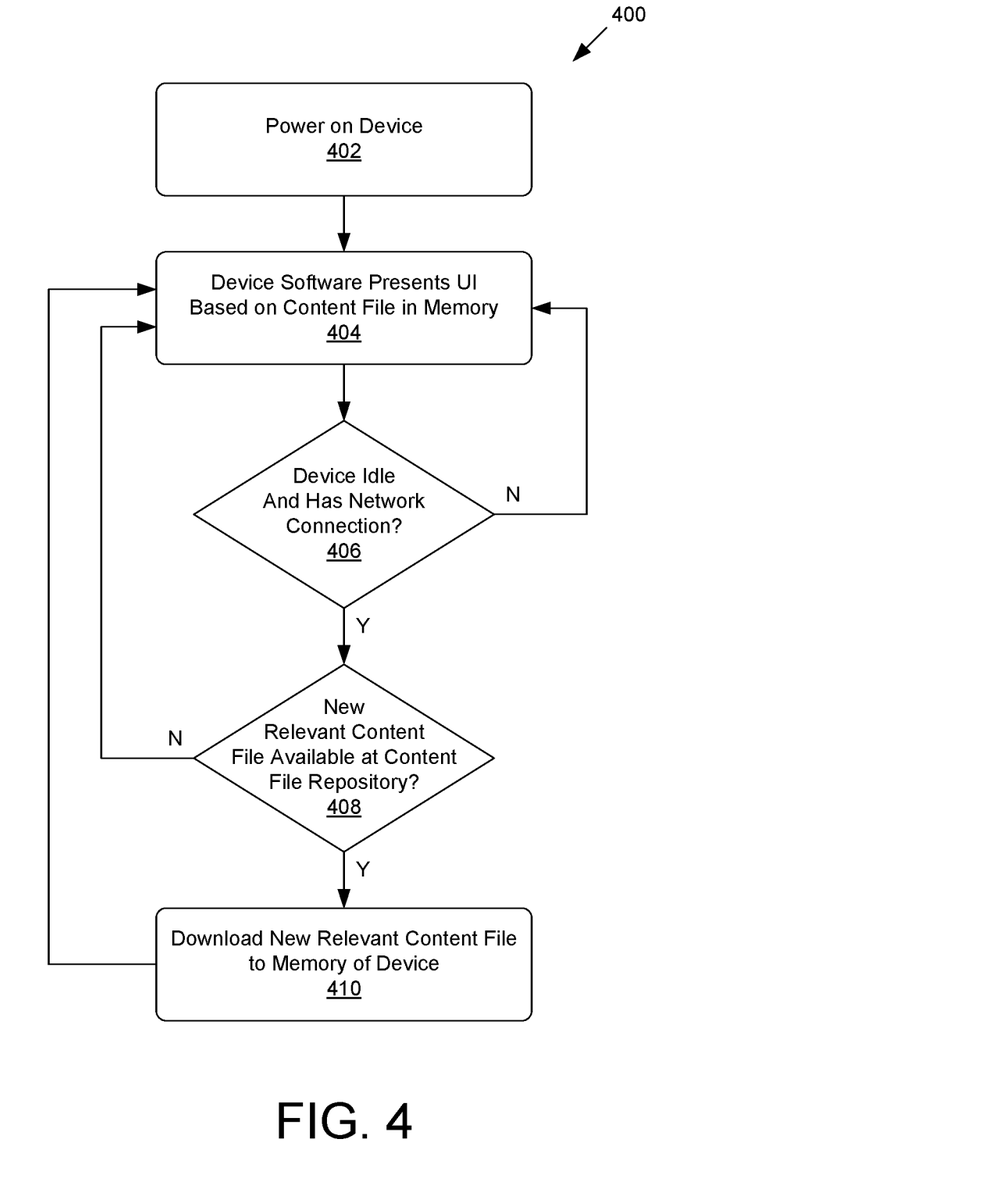
FIG. 4 shows a flowchart of an example process a device can use to download and use new content files.

Accordingly, as shown in FIGS. 3A-3C, the software 116 of a device can alter the content displayed in a user interface based on different content files 110. FIG. 4, discussed further below, shows an example process by which a device can obtain such different content files 110 from the content file repository 106.

FIG. 4 shows a flowchart 400 of an example process a device can use to download and use new content files. In this example process, the device can be configured to at least occasionally have access to the network 108 and the content file repository 106. For example, the communication interface 104 of the device can provide a wired or wireless data connection to a router or other network access point, such that the device can have a direct connection to the network 108. As another example, the communication interface 104 of the device can allow the device to be paired or tethered to a second device that has a connection to the network 108, such that the device can access the network 108 and the content file repository 106 when the device has a network connection via the second device.

The operations shown in FIG. 4 can be implemented by a computing device, such as one of the devices 102. For example, a computing device can use one or more processors to perform the operations shown in FIG. 4, based on computer-executable instructions executed by the one or more processors. The computing device that executes the operations shown in FIG. 4 can be a medical device or other types of embedded or constrained device that may be configured to perform specific functions, and that may have limited processing power and/or memory relative to general purpose computers or other types of computing devices. An example system architecture for such a computing device is discussed further below with respect to FIG. 5.

At block 402, the device can be powered on. Powering on the device can cause the software 116 of the device, such as firmware and/or applications, to boot or otherwise begin executing. The software 116 may accordingly begin presenting a user interface via the output element 120 associated with the device at block 404, and can determine content values to present in association with user interface elements based on at least one content file stored in memory 114 of the device. After the device is powered on at block 402, users may use the device for monitoring operations, diagnostic operations, or other operations of functions the device is configured to perform. In some examples, users can access and/or view information via the user interface presented at block 404 during use of the device, and/or interact with the device via the user interface presented at block 404.

At block 406, the device can determine whether the device is idle and has an active network connection. In some examples, the device can be configured to perform the operations of block 406 on a predefined schedule, such as once an hour, once a day, once a week, or on any other scheduled basis. The device can also, or alternately, be configured to perform the operations of block 406 in response to trigger events, such as the device being first powered on at block 402 (and before the device enters active use), the device becoming connected to the network 108, the device receiving a user instruction to check for updates to content files 110, or the device receiving a notification of new content files 110 from the content file repository 106.

If the device is not idle (Block 406—No), for instance if the device is in active use by a user, the device can return to block 404 to continue displaying the user interface and/or continue other operations of the device. Similarly, if the device is idle but does not have an active network connection (Block 406—No), the device can return to block 404 to continue displaying the user interface and/or continue other operations of the device. In some situations, if the device is idle, the device may enter a low-power state and/or temporarily cease displaying the user interface, but may remain ready to resume displaying the user interface when the device is next in active use.

However, if the device is idle and has an active network connection (Block 406—Yes), the device can query the content file repository 106 via the network 108 at block 408 to determine whether a new relevant content file 110 is available at the content file repository 106. A relevant content file can be a replacement for a content file that is already stored in memory 114 of the device, or a content file associated with a language or other type of content that is likely to be used by the device to present a user interface.

For example, the device can query the content file repository 106 to determine if the content file repository 106 has a newer version of a content file that is currently stored in memory of the device. For instance, if the memory 114 stores a first version of an English-language content file, the device can determine at block 408 whether a newer version of the English-language content file is available at the content file repository 106.

As another example, the device can query the content file repository 106 to determine if another content file that is relevant to the device is available at the content file repository 106. For instance, if the memory 114 of the device stores an English-language content file, but location information, user settings, or other data indicates that the device is located in an area where a different language is predominantly spoken, the device can query the content file repository 106 to determine whether a content file associated with that different language is available. As a non-limiting example, the device may determine or estimate a location of the device based on GPS coordinates, an IP address assigned to the device, device registration data, and/or other data. The device may use that location information to determine a language that corresponds to the location of the device, or provide the location information to the content file repository 106, such that the device can determine whether the content file repository 106 stores a content file associated with the language that corresponds to the location of the device.

If a new relevant content file is not available at the content file repository 106 (Block 408—No), the software 116 of the device can continue using one or more content files 110 already stored in the memory 114 of the device to present the user interface at block 404. At later points in time, the device may automatically perform checks for new relevant content files 110 at the content file repository 106, for instance at later times when the device is again idle and has a network connection.

If a new relevant content file is available at the content file repository 106 (Block 408—Yes), the device can download the new relevant content file to memory 114 at block 410. The software 116 of the device can use the content file downloaded at block 410 to present the user interface at block 404, for instance by changing and/or determining content displayed in association with one or more user interface elements based on corresponding content values indicated in the newly downloaded content file. The software 116 itself can continue to execute without modification, but can use the newly downloaded content file to determine content values to present in association with user interface elements. For example, the software 116 can directly use the content file newly downloaded at block 410 to determine content values to present in association with corresponding user interface elements, without the software 116 itself being reloaded or upgraded, and without the device being restarted. At later points in time, the device may again automatically perform a check for additional new relevant content files 110 at the content file repository 106, for instance at later times when the device is again idle and has a network connection.

Figure 5:
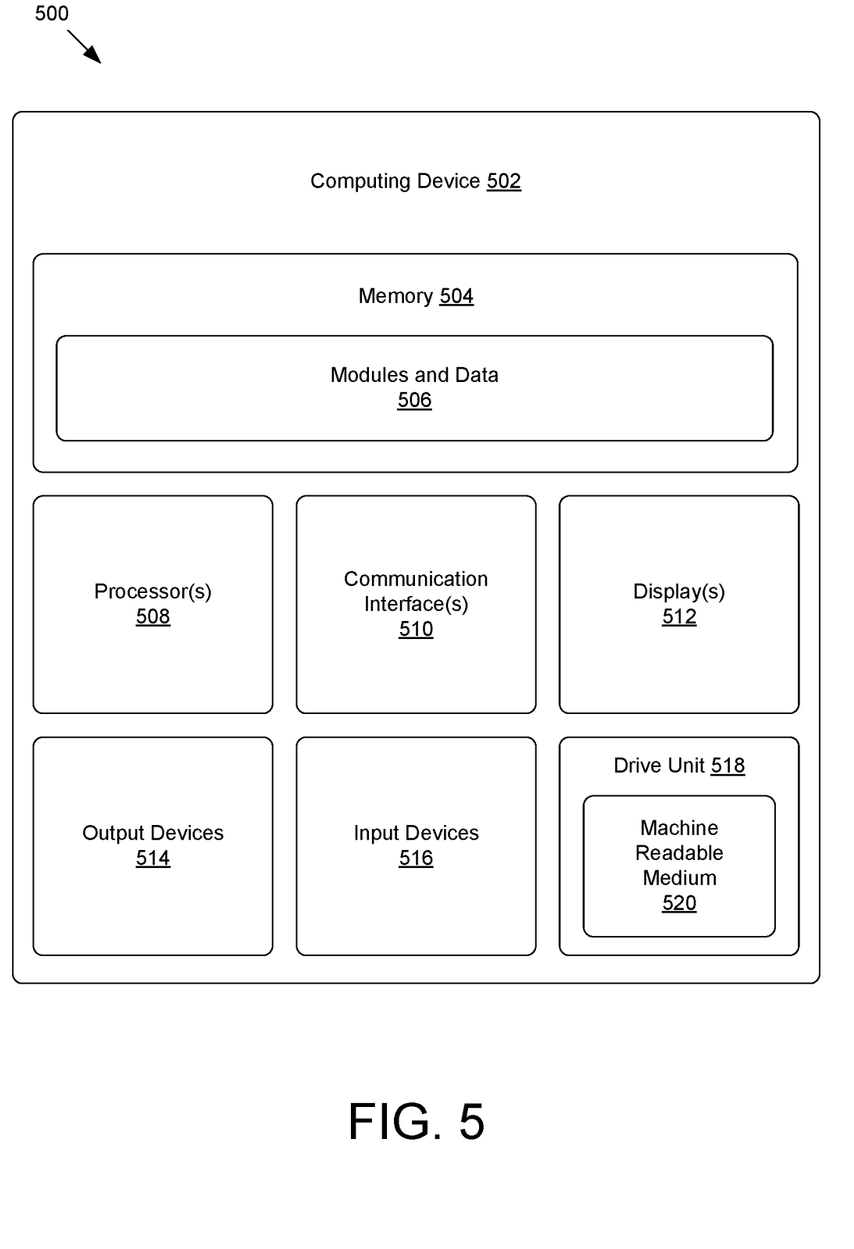
FIG. 5 shows an example system architecture for a computing device.

FIG. 5 shows an example system architecture 500 for a computing device 502 associated with the systems and methods described herein. The computing device 502 can be a server, computer, or other type of computing device that executes one or more portions of the systems and methods described herein. In some examples, the computing device 502 can be a server or other computing device that stores and/or implements the content file repository 106. In other examples, the computing device 502 can be an example of one of the devices 102 that can receive content files 110 from the content file repository 106 and can use the content files 110 to present user interfaces.

The computing device 502 can include memory 504. In various examples, the memory 504 can include system memory, which may be volatile (such as RAM), non-volatile (such as ROM, flash memory, etc.) or some combination of the two. The memory 504 can further include non-transitory computer-readable media, such as volatile and nonvolatile, removable and non-removable media implemented in any method or technology for storage of information, such as computer readable instructions, data structures, program modules, or other data. System memory, removable storage, and non-removable storage are all examples of non-transitory computer-readable media. Examples of non-transitory computer-readable media include, but are not limited to, RAM, ROM, EEPROM, flash memory or other memory technology, CD-ROM, digital versatile discs (DVD) or other optical storage, magnetic cassettes, magnetic tape, magnetic disk storage or other magnetic storage devices, or any other non-transitory medium which can be used to store desired information and which can be accessed by the computing device 502. Any such non-transitory computer-readable media may be part of the computing device 502.

The memory 504 can store modules and data 506. The modules and data 506 can include modules and/or data that can be utilized by the computing device 502 to perform or enable performing any action taken by the computing device 502. Such modules and data can include a platform, operating system, and applications, and data utilized by the platform, operating system, and applications. For example, if the computing device 502 hosts the content file repository 106, the modules and data 506 can include the content files 110, modules and data for uploading new content files 110 to the content file repository 106, modules and data that allow devices to query the content file repository 106 for relevant content files 110 and to download content files 110, and/or other modules and data. As another example, if the computing device 502 is one of the devices 102, the modules and data 506 can include one or more content files 110 stored by the device, the software 116 that implements functions of the device and/or that presents a user interface based on the content files 110, modules and data for querying the content file repository 106 for new relevant content files 110 and/or to download or receive new relevant content files 110, and/or other modules and data.

The computing device 502 can also have processor(s) 508, communication interfaces 510, a display 512, output devices 514, input devices 516, and/or a drive unit 518 including a machine readable medium 520.

In various examples, the processor(s) 508 can be a central processing unit (CPU), a graphics processing unit (GPU), both a CPU and a GPU, or any other type of processing unit. Each of the one or more processor(s) 508 may have numerous arithmetic logic units (ALUs) that perform arithmetic and logical operations, as well as one or more control units (CUs) that extract instructions and stored content from processor cache memory, and then executes these instructions by calling on the ALUs, as necessary, during program execution. The processor(s) 508 may also be responsible for executing computer applications stored in the memory 504, which can be associated with types of volatile (RAM) and/or nonvolatile (ROM) memory.

The communication interfaces 510 can include transceivers, modems, interfaces, antennas, telephone connections, and/or other components that can transmit and/or receive data over networks, telephone lines, or other connections.

The display 512 can be a liquid crystal display, or any other type of display commonly used in computing devices. For example, a display 512 may be a touch-sensitive display screen, and can then also act as an input device or keypad, such as for providing a soft-key keyboard, navigation buttons, or any other type of input.

The output devices 514 can include any sort of output devices known in the art, such as a display 512, speakers, a vibrating mechanism, and/or a tactile feedback mechanism. Output devices 514 can also include ports for one or more peripheral devices, such as headphones, peripheral speakers, and/or a peripheral display.

The input devices 516 can include any sort of input devices known in the art. For example, input devices 516 can include a microphone, a keyboard/keypad, and/or a touch-sensitive display, such as the touch-sensitive display screen described above. A keyboard/keypad can be a push button numeric dialing pad, a multi-key keyboard, or one or more other types of keys or buttons, and can also include a joystick-like controller, designated navigation buttons, or any other type of input mechanism.

The machine readable medium 520 can store one or more sets of instructions, such as software or firmware, that embodies any one or more of the methodologies or functions described herein. The instructions can also reside, completely or at least partially, within the memory 504, processor(s) 508, and/or communication interface(s) 510 during execution thereof by the computing device 502. The memory 504 and the processor(s) 508 also can constitute machine readable media 520.

As discussed above, in some examples the computing device 502 can be an example of one of the devices 102. The devices 102 can be embedded devices or constrained devices, such as medical devices, that are configured to perform particular functions. In these examples, the memory 504, processor(s) 508, and/or other elements of the computing device 502 may be more limited and/or less powerful than memory, processors, and/or other elements of general purpose computers, smartphones, or other types of computing devices. For instance, the memory 504 may have a relatively small amount of storage space that can store data associated with the software 116 and/or other computer-executable instructions executed by the processors 508, as well as one content file, two content files, three content files, or any other relatively small number of content files 110, but may not have sufficient space to store larger numbers of content files 110. However, as described above, computer-executable instructions executed by the processors 508 can determine which content files 110 are to be stored in the memory 504, and/or determine when to update the content files 110 stored in the memory 504.

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:

1. A method comprising:
determining, via software executing on a medical device, a user interface element to display in a user interface of the medical device, wherein:
the software is coded with a content identifier that corresponds to the user interface element, and
the user interface element is configured to present a content value defined by a content file;
presenting, via the software, and in the user interface element, a first predefined content value that a first content file, stored in memory of the medical device, indicates is associated with the content identifier;
loading a second content file into the memory of the medical device during execution of the software, wherein the second content file:
is provided by a content file repository remote from the medical device, and
indicates a second predefined content value that is associated with the content identifier; and
updating, via the software, the content value, presented in the user interface element, from the first predefined content value to the second predefined content value based on the second content file,
wherein the content value presented in the user interface element is updated, based on the second content file, without upgrading the software, restarting the software on the medical device, or rebooting the medical device.

2. The method of claim 1, wherein:
the first predefined content value, indicated by the first content file, comprises a first text string expressed in a language, and
the second predefined content value, indicated by the second content file, comprises a second text string expressed in the language.

3. The method of claim 1, wherein:
the first predefined content value, indicated by the first content file, comprises a first text string expressed in a first language, and
the second predefined content value, indicated by the second content file, comprises a second text string expressed in a second language.

4. The method of claim 3, wherein the second language is associated with a location of the medical device that is automatically determined by at least one of the medical device or the content file repository.

5. The method of claim 4, wherein the location of the medical device is automatically determined based on at least one of Global Positioning System (GPS) coordinates of the medical device or an Internet Protocol (IP) address assigned to the medical device.

6. The method of claim 1, wherein loading the second content file comprises:
determining, via the software executing on the medical device, that the medical device is idle and has a connection to a network;
querying, via the software executing on the medical device, and over the network, the content file repository for content files relevant to the medical device;
determining, via the software executing on the medical device, that the second content file is relevant to the medical device; and
downloading, by the medical device over the network, the second content file to the memory of the medical device.

7. The method of claim 1, wherein the medical device is a constrained device and the memory is configured to store up to a maximum number of content files.

8. The method of claim 1, wherein the content value comprises at least one of a graphical element, audio data, or animation data.

9. The method of claim 1, wherein the user interface element comprises one of:
a user interface button that is selectable by a user to initiate corresponding functionality coded in the software,
a title bar for a section of the user interface, or
a logo of a manufacturer of the medical device.

10. The method of claim 1, wherein the user interface element:
is a static component of the user interface, and
is distinct from a dynamic element, displayed within the user interface, that is configured to display patient data determined via local operations of the medical device.

11. A medical device comprising:
one or more processors; and
memory storing computer-executable instructions associated with software that, when executed by the one or more processors, cause the one or more processors to perform operations comprising:
determining a user interface element to display in a user interface of the medical device, wherein:

the software is coded with a content identifier that corresponds to the user interface element, and the user interface element is configured to present a content value defined by a content file;

presenting, via the user interface element, a first predefined content value that a first content file, stored in the memory, indicates is associated with the content identifier;

loading a second content file into the memory, wherein the second content file:

is provided by a content file repository remote from the medical device, and indicates a second predefined content value that is associated with the content identifier; and updating the content value, presented via the user interface element, from the first predefined content value to the second predefined content value based on the second content file, wherein the content value presented via the user interface element is updated, based on the second content file, without upgrading the software, restarting the software on the medical device, or rebooting the medical device.

12. The medical device of claim 11, wherein the medical device comprises a communication interface, and loading the second content file comprises:

determining that the medical device is idle and has a connection to a network via the communication interface;

querying, over the network via the communication interface, the content file repository for content files relevant to the medical device;

determining that the second content file is relevant to the medical device; and downloading, over the network via the communication interface, the second content file to the memory.

13. The medical device of claim 11, wherein:

loading the second content file comprises transferring the second content file from a removable storage unit or an intermediate computing device connected to the medical device, and the second content file was downloaded from the content file repository and stored on the removable storage unit or the intermediate computing device.

14. The medical device of claim 11, wherein the content value comprises at least one of a text string, a graphical element, audio data, or animation data.

15. The medical device of claim 11, wherein the medical device is a constrained device and the memory is configured to store up to a maximum number of content files.

16. One or more non-transitory computer-readable media storing computer-executable instructions that, when executed by one or more processors of a medical device, cause the one or more processors to perform operations comprising:

determining a user interface element to display in a user interface associated with the medical device, wherein the user interface element is configured to display a content value, defined by a content file, that is associated with a content identifier;

displaying, at a first time, and via the user interface element, a first predefined content value that a first content file, stored locally on the medical device, indicates is associated with the content identifier;

receiving a second content file, downloaded from a content file repository, indicating a second predefined content value that is associated with the content identifier; and updating, at a second time, and based on the second content file, the content value displayed via the user interface element, from the first predefined content value to the second predefined content value, without rebooting the medical device or changing the computer-executable instructions.

17. The one or more non-transitory computer-readable media of claim 16, wherein:

the first predefined content value, indicated by the first content file, comprises a first text string expressed in a language, and the second predefined content value, indicated by the second content file, comprises a second text string expressed in the language.

18. The one or more non-transitory computer-readable media of claim 16, wherein:

the first predefined content value, indicated by the first content file, comprises a first text string expressed in a first language, and the second predefined content value, indicated by the second content file, comprises a second text string expressed in a second language.

19. The one or more non-transitory computer-readable media of claim 16, wherein the content value comprises at least one of a graphical element, audio data, or animation data.

20. The one or more non-transitory computer-readable media of claim 16, wherein receiving the second content file comprises:

determining that the medical device is idle and has a connection to a network;

querying, via the network, the content file repository for content files relevant to the medical device;

determining that the second content file is relevant to the medical device; and downloading the second content file from the content file repository to the medical device via the connection to the network.

\* \* \* \* \*